US00PP35492P3

(12) United States Plant Patent
Shipley

(10) Patent No.: US PP35,492 P3
(45) Date of Patent: Nov. 21, 2023

(54) ***ASCLEPIAS LINARIA* PLANT NAMED 'MONARCH MAGNET 2.0'**

(50) Latin Name: *Asclepias linaria*
Varietal Denomination: Monarch Magnet 2.0

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 262 days.

(21) Appl. No.: 16/974,126

(22) Filed: Oct. 14, 2020

(65) Prior Publication Data

US 2022/0256753 P1 Aug. 11, 2022

(51) Int. Cl.
*A01H 6/08* (2018.01)
*A01H 6/00* (2018.01)
*A01H 5/02* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 6/08; A01H 5/02
See application file for complete search history.

*Primary Examiner* — Keith O. Robinson

(57) ABSTRACT

A new and distinct *Asclepias linaria* plant named 'Monarch Magnet 2.0' is characterized by denser and fuller plant form and greater resistance of sudden death from damping-off than is typical for the species.

10 Drawing Sheets

Latin name: *Asclepias linaria.*
Varietal denomination: Monarch Magnet 2.0.

BACKGROUND OF THE INVENTION

*Asclepias linaria*, pineleaf milkweed, is a semiwoody shrub mostly associated with the evergreen oak vegetation complex of the middle elevations of southern Arizona, southwest New Mexico and the adjacent Mexican states of Sonora and Chihuahua, growing from 1500-6000 feet in elevation.

Pineleaf milkweed has been utilized as a landscape shrub in the lower elevations of Arizona for probably around 40 years mostly as unselected seedling plants originally wild collected. The plants generally present a rather open form typically about 3 feet tall by as much as 4 feet wide. Whitish flowers are produced throughout the warm season, followed by fleshy fruits that dry out to disperse wind borne seeds. Pineleaf milkweed is a larval food plant for monarch and queen butterflies as well as a butterfly and bee attracting nectar plant.

The present invention relates to a new and distinct cultivar of pineleaf milkweed, *Asclepias linaria*. The cultivar originated as a chance seedling from nursery saved seed from an open pollinated *Asclepias linaria* 'Monarch Magnet'. The plant has a slightly tighter, denser appearance and a very strong resistance to damping off diseases than is typical of the species and is the object of this application. There appears to be no existing named cultivars outside of the original Monarch Magnet variety.

SUMMARY OF THE INVENTION

Among the features that distinguish the new *Asclepias linaria* cultivar from all other available and commercial varieties of *Asclepias linaria* known to the inventor is the following combination of characteristics: a tighter, denser appearance due to an increased tendency to produce a higher degree of branching all along the main stems and a much greater resistance to sudden death from damping off compared to other available related pineleaf milkweed plants.

The asexual propagation procedure is as follows: Three inch long semihardwood cuttings are prepared and the bottom 1" is stripped of leaves. Fresh cuts are placed into a 1:10 solution of an auxin type formulation called DIP'NGRO™ for 5 minutes, then planted in peat based media in grow trays. These are moved to a mist greenhouse with mist applications every 15 minutes at temperatures between 65-78° F. until rooting is complete, which typically takes about 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Asclepias linaria* 'Monarch Magnet 2.0' growing near Tucson, Arizona, depicted in color as nearly correct as it is possible to make in a color illustration of the character.

DETAILED PLANT DESCRIPTION

Figure 1:
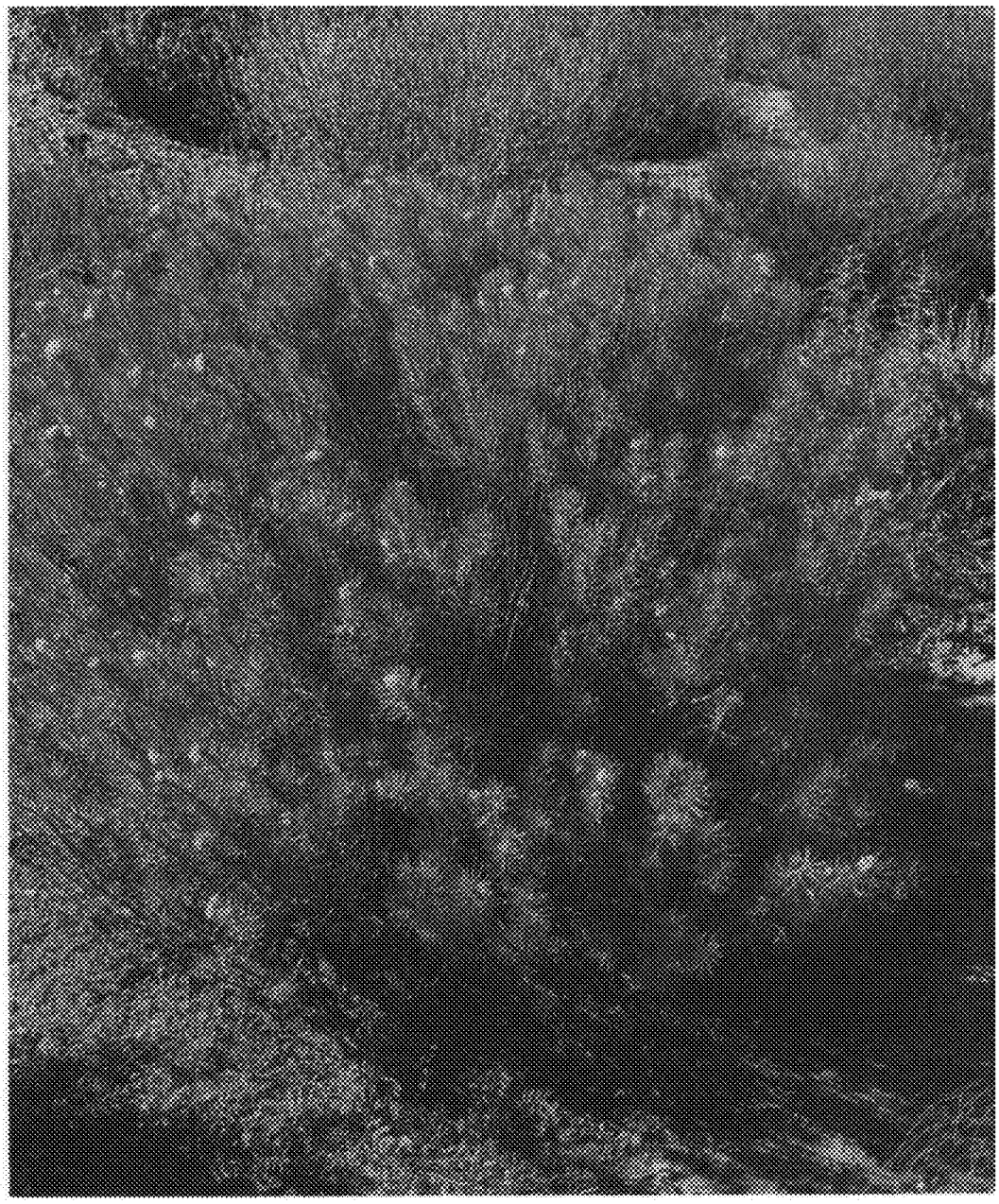
FIG. 1 shows *Asclepias linaria* 'Monarch Magnet 2.0' growing at a commercial nursery near Sahuarita, AZ at age 3.
Figure 2:
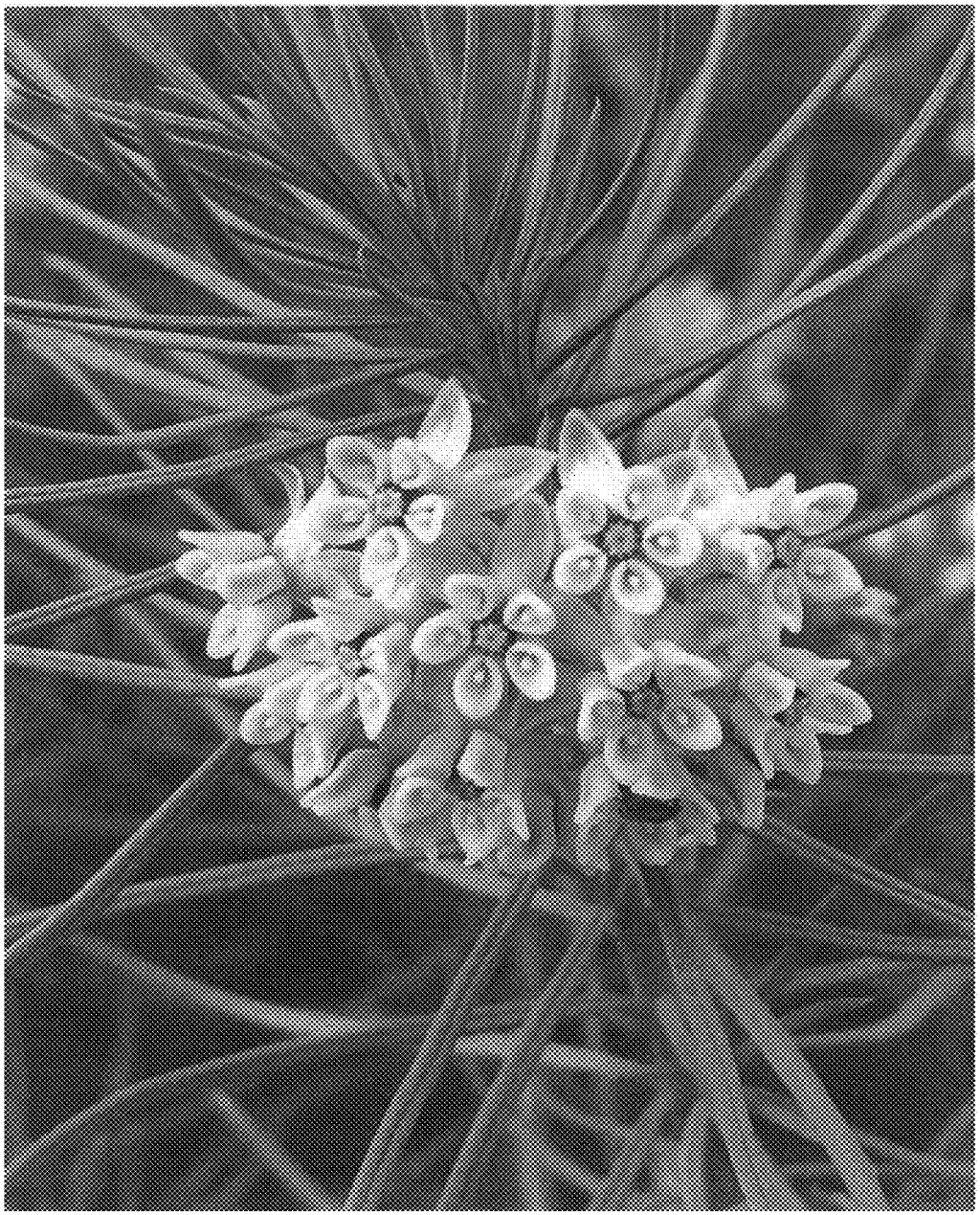
FIG. 2 shows *Asclepias linaria* 'Monarch Magnet 2.0' inflorescence and leaves.
Figure 3:
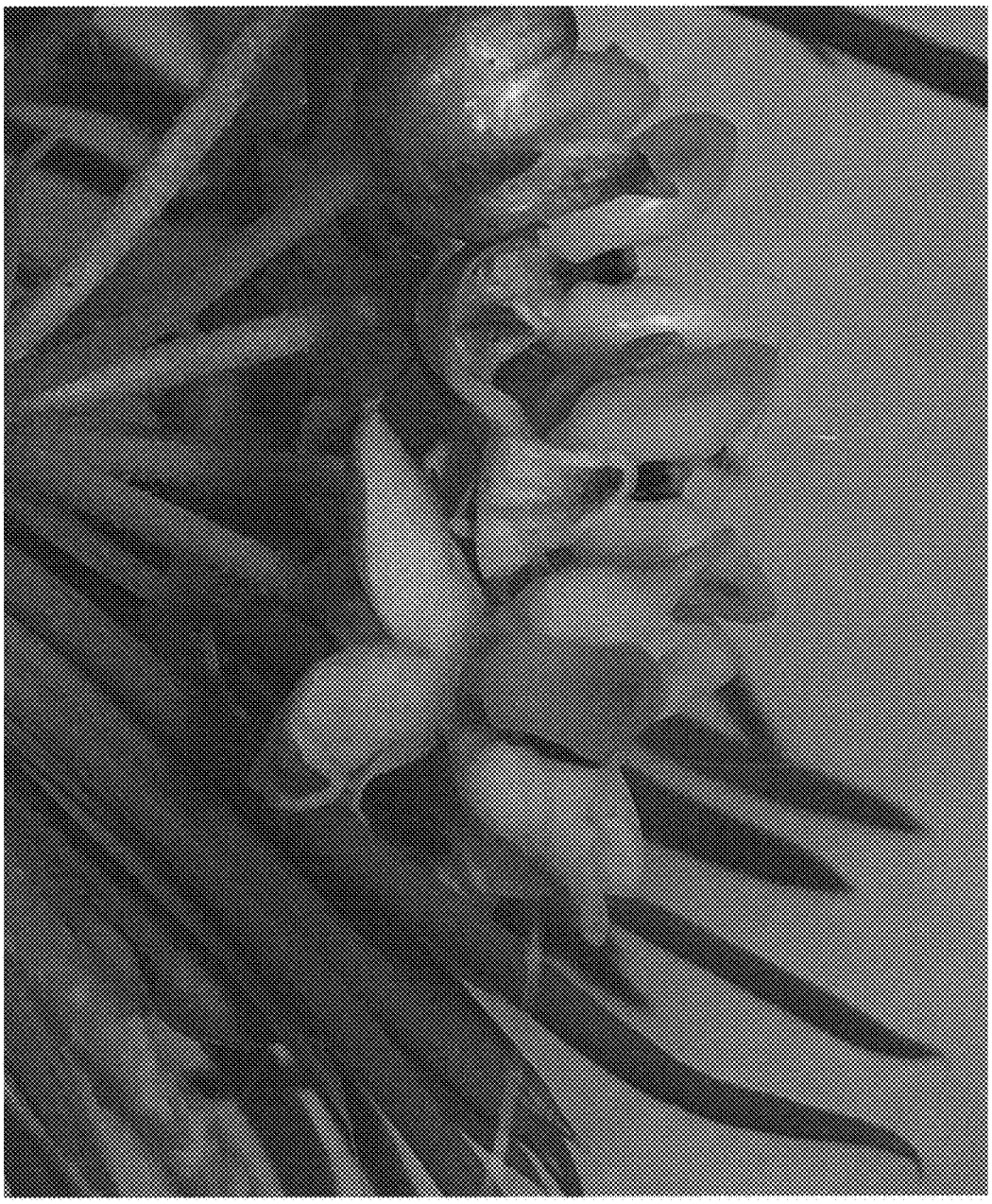
FIG. 3 shows *Asclepias linaria* 'Monarch Magnet 2.0' flowers.
Figure 4:
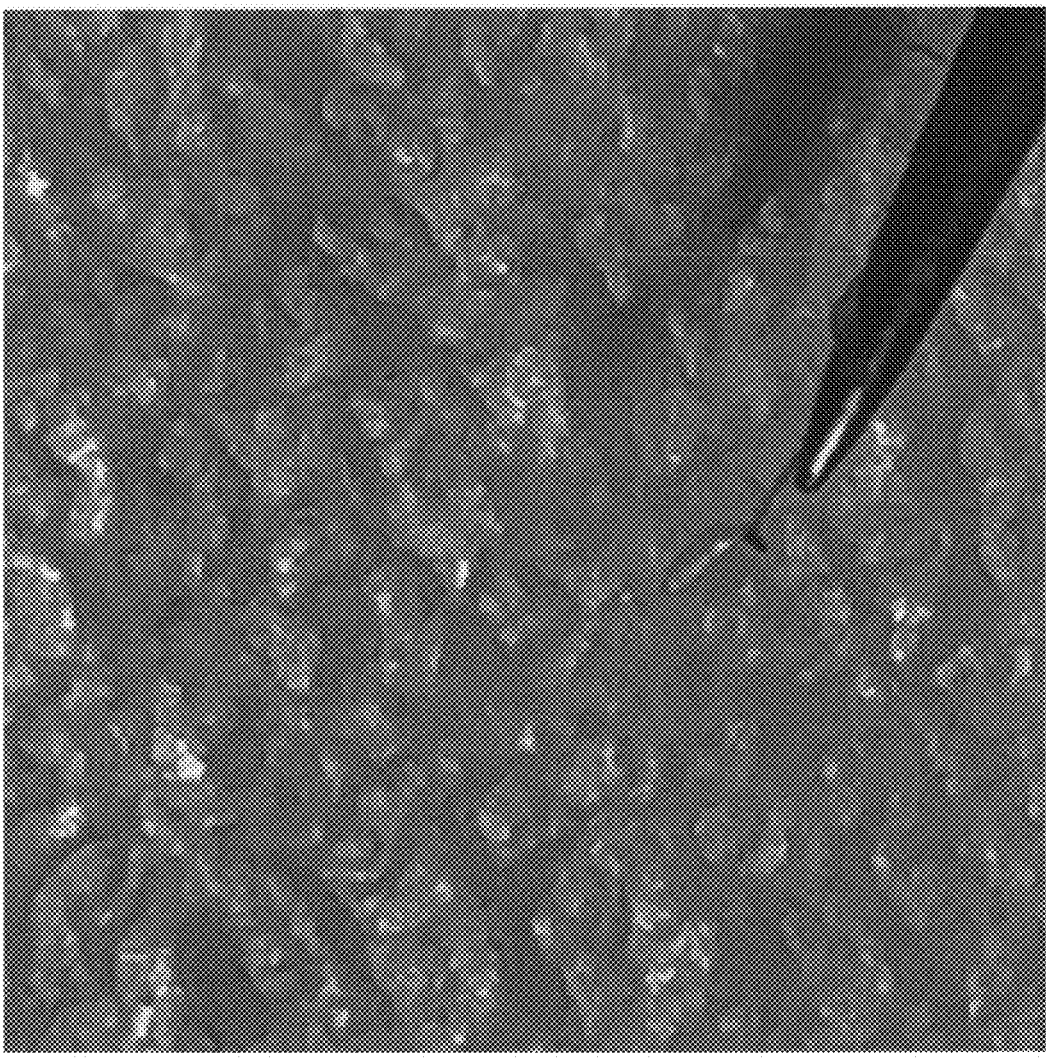
FIG. 4 shows a pair of Pollinia from an *Asclepias linaria* 'Monarch Magnet 2.0' flower.
Figure 5:
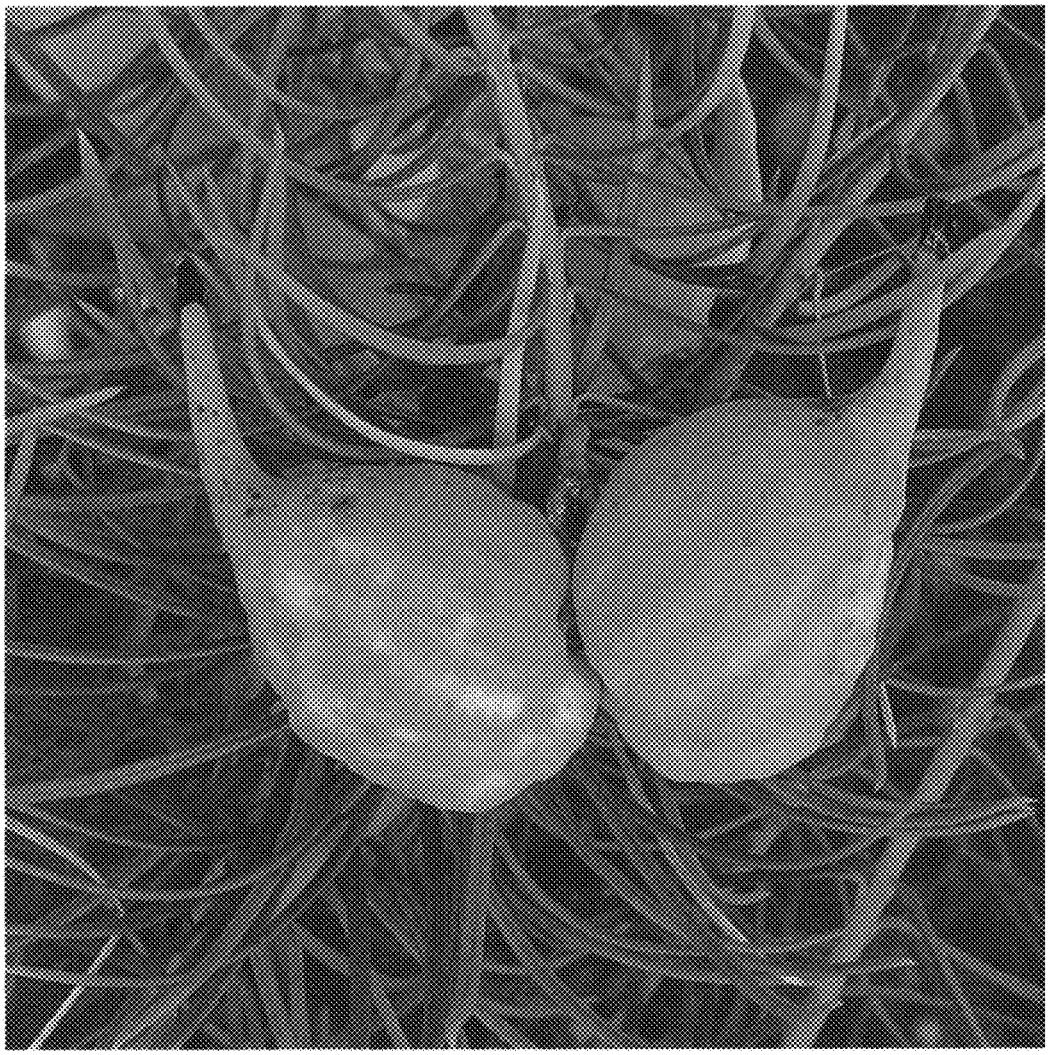
FIG. 5 shows a pair of *Asclepias linaria* 'Monarch Magnet 2.0' fruits.
Figure 6:
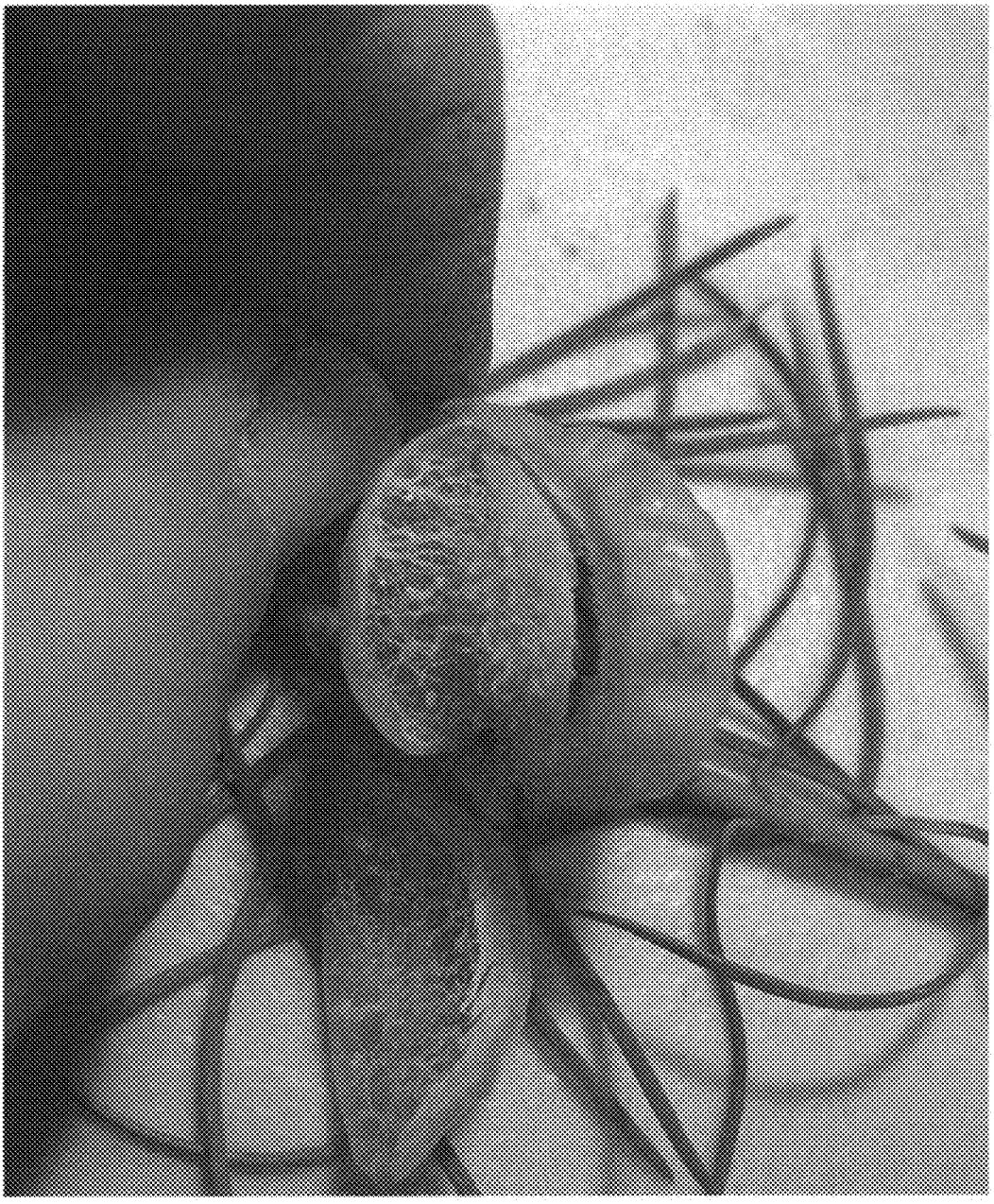
FIG. 6 is a photograph showing the spongy interior of the fruit wall of *Asclepias linaria* 'Monarch Magnet 2.0'.
Figure 7:
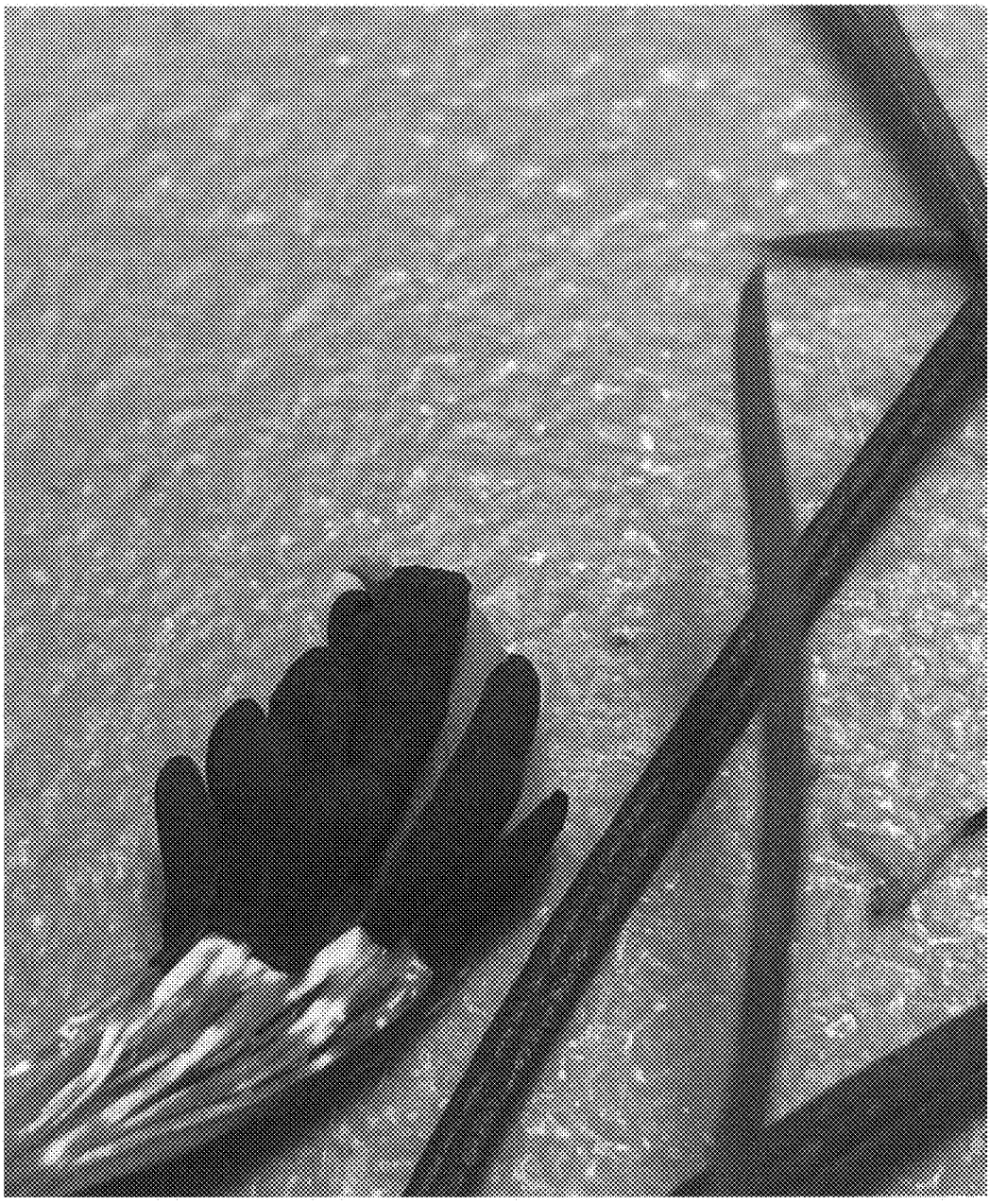
FIG. 7 illustrates the moist seeds of *Asclepias linaria* 'Monarch Magnet 2.0' attached to the placenta.
Figure 8:
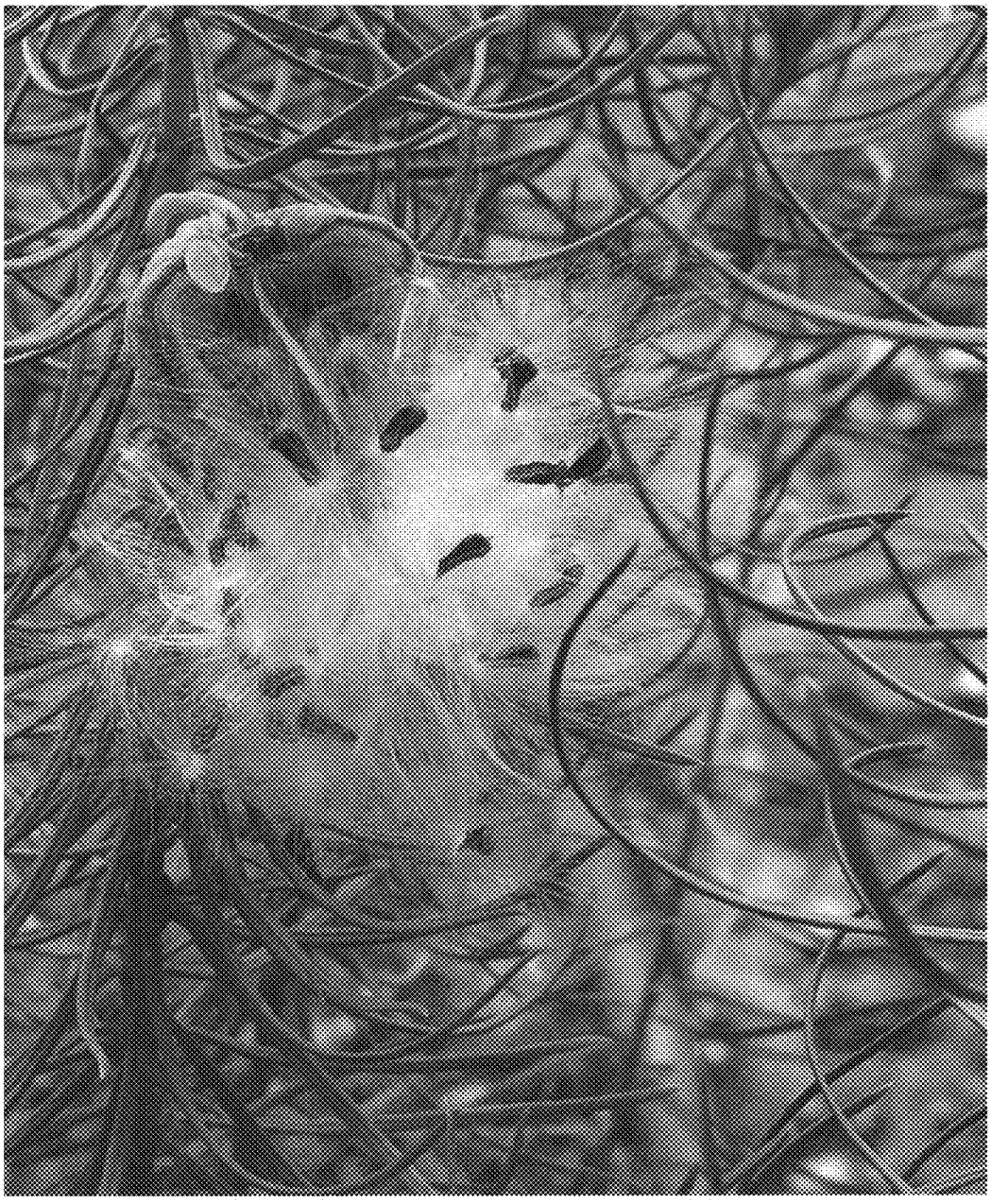
FIG. 8 shows a dehisced fruit of *Asclepias linaria* 'Monarch Magnet 2.0' with seeds and coma ready to wind disperse.
Figure 9:
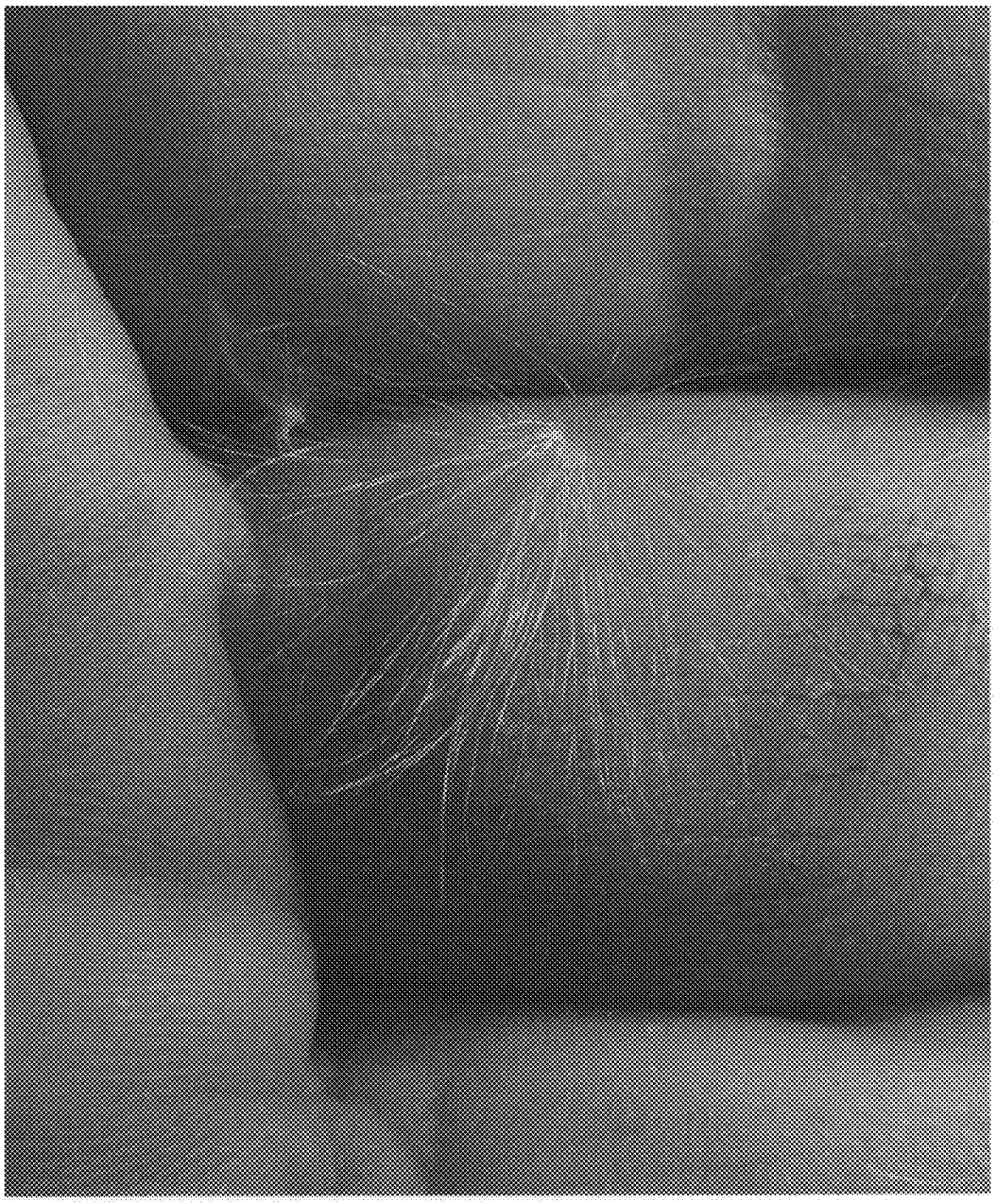
FIG. 9 is a closeup of a couple of comas detached from their seeds.
Figure 10:
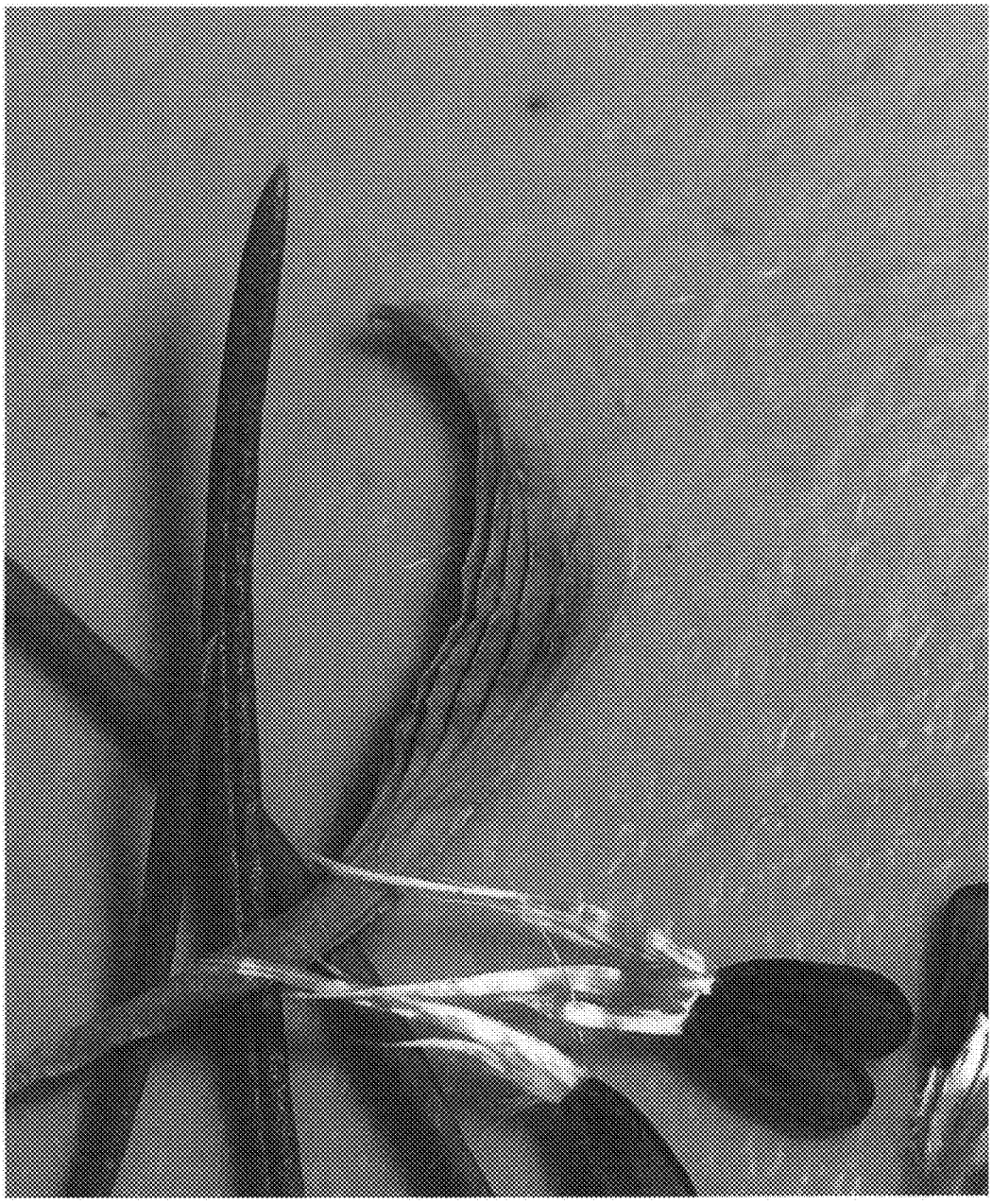
FIG. 10 shows a fruit placenta and moist seeds from *Asclepias linaria* 'Monarch Magnet 2.0'.

The following is a detailed description of the new *Asclepias linaria* plant based upon a one year old plant propagated by cutting and growing in a 5 gallon nursery pot and the originally selected 3 year old plant growing in the ground at a commercial nursery near Sahuarita, Arizona. The color descriptions are based upon the 5$^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant a basally woody, apically herbaceous, leafy, many branched shrub growing up to 3 ft tall×3.5 ft wide at maturity. Plants branch heavily near ground level and branching continues into the upper portions of the plant. Branch angles vary from 30-60°. Branching is mostly alternate, but some alternate branching occurs.

'Monarch Magnet 2.0' has a moderate growth rate and is moderately vigorous. 'Monarch Magnet' is hardy to 12° F., USDA hardiness zone 8. 'Monarch Magnet' normally blooms from May to October under conditions at Sahuarita, Arizona.

Stems are terete, of medium strength, basally woody grading to suffrutescent and finally to herbaceous above. Young stems measure from 1-2.5 mm in diameter and are covered with very fine, mostly appressed and forward pointing hairs that are caducous with maturation. Internodes vary in length from 1-20 mm in length. Stem color at this stage of development closest to 144A. Stems thicken with age and the color also gradually changes to 152D by the time the stems reach 3-4 mm in diameter. Stems continue to thicken with age and the color finally grades to 197C by the time the stems reach 6-7 mm in diameter, which is close to the maximum stem diameter.

Leaves are sessile (without petioles) and vary in arrangement from alternate to opposite, with most of them alternate in arrangement. Leaves are simple, linear with a downward thickening at the leaf margins with a prominent midrib, color 138B. The midrib is indented on the adaxial surface and bulging on the abaxial surface. The midrib is glabrous and somewhat lustrous. Leaf adaxial surface has scattered relatively upright to appressed hairs when young, these soon caducous, the leaf becoming glabrous, color 138A at maturity. Leaf margins are colored 138A. The abaxial surface is glabrous and colored 138B. The leaf apex is apiculate. Leaves measure 1.5-2 mm wide×36-56 mm long. The leaf base is linear, slightly acute. Venation is obscure.

Inflorescence is umbellate with each umbel bearing 5-20 flowers. Peduncles measure 6 mm long×1.5 mm diameter, terete, colored 145C at anthesis. Plants growing in full sun have peduncles tinged with 184A on the sunward side as well as just below the involucre. The peduncle thickens as the fruits develop.

Involucre consists of a ring of 8-10 lance linear leafy bracts (color 138B) measuring about 4 mm long×1 mm wide. The involucre bracts are caducous close to the time of anthesis; generally these are completely shed by the time the last flowers of an inflorescence open.

Umbels (inflorescences) measure 15-35 mm in diameter× 13-15 mm long not including the peduncle. Umbels are hemispherical in shape. Inflorescences will have active flowering for up to several weeks, depending upon temperatures and pollination status. After pollination of one to several flowers the remaining flowers and buds will abort within about a week.

The pedicels measure 8-9 mm long×1 mm in diameter at anthesis, colored 145C. Brightly lit plants have pedicels tinged with 184A on the sunward side. Pedicels are loosely covered with fine spreading to ascending hairs visible under magnification, these soon caducous.

Buds are spherical, measuring 3 mm in diameter. Most of the bud is colored 145D. The apex is colored 59A. The bud is glabrous.

Flowers measure 8-10 mm in diameter and 5-7 mm in length. The flower has spreading petals with a crown shaped corona. The overall shape is roughly ovoid. No fragrance was noted. Individual flowers last about a week unless pollinated, which decreases lastingness.

Calyx 5-merous, spreading, somewhat united at the receptacle, but sepals mostly free. Sepals measure 2.5 mm long× 1.25 mm wide, colored mostly N144C with the tips of the sepals colored 61A. Sepals are lanceolate, apiculate, covered with fine sparse ascending hairs abaxially, glabrous adaxially. Sepals somewhat cupped to the adaxial side and are more or less carinate.

Corolla 5-merous, radially spreading, somewhat reflexed, mostly colored 157D. Petals are somewhat carinate, more or less lanceolate, fused basally, measuring 3-4 mm long×2 mm wide with a mid-petal crease to the adaxial side. Abaxial side of petals are colored 59A near the petal apex and along about the upper ⅓ of the petal crease transitioning gradually to the primary petal color 157D. Adaxial petal surface is colored 157D. Petals are glabrous.

Hoods 5, measuring 4 mm long×2 mm wide, ascending, spreading at the apex, very nectiferous. Hoods are colored close to 157B with an abaxial vein colored 145C. Hoods are slit on the adaxial side. Horns are colored like the hoods, terete, rounded at the tip, not hooked, about 0.3 mm in diameter, firmly attached to the receptacle basally, more or less clublike.

Gynostegium measures 1.75 mm long×1.5 mm diameter. Sides of the gynostegium other than the veils are colored N187A. Veils are basally nose shaped projecting outward at the base of the gynostegium, colored 153C, and the margins colored 184A. The apex of the gynostegium is radially 10 pointed, the points paired and more or less flattened. The apex has a central funnel shaped depression. The gynostegium apex is colored 145C.

Pollinia are paired, each measuring 1 mm long×0.25 mm wide×0.05 mm thick and more or less oblong in shape, translucent and colored 163C.

Ovaries paired, essentially free from each other, capable of forming paired follicles, although it is uncommon for both ovary lobes to develop. Ovaries measure 1.75 mm long×1 mm in diameter. The ovary basal portion is more or less spheroid except flattened between the two ovary bases. Basal portion of ovary measures 1 mm. Close to the apex of each ovary base the ovary rather abruptly narrows to 0.33 mm in diameter. The upper portion of the ovary is essentially a narrowing cone with a rounded tip. This portion measures 0.75 mm long×0.33 mm in diameter. Ovaries are colored 138C basally grading to 1380 near the apex of the conical portion. Fruit is an inflated follicle frequently appearing paired, although most apparent pairs are attached to separate pedicels. Mature follicles measure from about 28-46 mm long×20-26 mm in diameter, their shape mostly ovoid, with a tapering upreaching rounded point. Fruits are mostly colored 145A with faint longitudinal bands colored 145C. Bands colored 145A measure 2-5 mm wide, while those colored 145C measure 1.5-2 mm wide. The fruit surface is glabrous and irregularly bumpy. Fruits located in deeply shaded portions of the plant can be as light in color as 145D. These fruits tend to be uniform in color without banding. The fruit wall is thickened and spongy in cross section, thinning out as the fruit dries.

Fruits dry and dehisce at maturity on one longitudinal line on the adaxial side. The color of the dry fruit varies from 164A-164D with no discernable pattern other than as noted below. The color of the fruit along the dehiscence margins and the fruit tail is generally closer to 164A-164B. Also notable is a color band opposite the dehiscence line near the widest part of the fruit 164D.

Fruits contain about 30 seeds each, these overlapping like fish scales attached to the placenta. Seeds are flattened and more or less obovate, measuring 4-5 mm long×2 mm wide×1 mm thick, somewhat cupped toward the placental side, colored 165A. A coma is attached at the base of each seed, which make the seeds easily wind dispersed. Coma consists of 20-30 fine white (whiter than NN155C) hairs that measure from 7 mm-2 cm in length.

The placenta is obfalcate in shape, more or less matching the fruit in shape and size, measuring from 28-40 mm long×3-4 mm wide×1.5-2.0 mm thick. The placenta is distinctly longitudinally grooved in the fertile area on the flattened sides. The placenta varies in color from 164B to 164D, closest to 164B in the fertile area, gradually lightening ultimately to 164D in the parts furthest from the fertile area.

COMPARISONS TO RELATED *ASCLEPIAS LINARIA*

Compared to typical seed grown nursery stock of *Asclepias linaria*, 'Monarch Magnet 2.0' presents a denser, fuller plant due to its increased branching tendency.

Compared to the superficially similar cultivar, 'Monarch Magnet', 'Monarch Magnet 2.0' has a slightly tighter, denser growth habit. 'Monarch Magnet 2.0' also has improved resistance to damping off fungi compared to 'Monarch Magnet'.

I claim:

1. A new and distinct *Asclepias linaria* plant named 'Monarch Magnet 2.0' substantially as described and illustrated herein.

* * * * *